United States Patent
Sucha et al.

(10) Patent No.: US 6,723,991 B1
(45) Date of Patent: Apr. 20, 2004

(54) SINGLE-SHOT DIFFERENTIAL SPECTROSCOPY AND SPECTRAL-IMAGING AT SUBMILLIMETER WAVELENGTHS

(75) Inventors: Gregg D. Sucha, Manchester, MI (US); Donald J. Harter, Ann Arbor, MI (US); Almantas Galvanauskas, Ann Arbor, MI (US)

(73) Assignee: Imra America, Inc., Ann Arbor, MI (US)

( * ) Notice: Subject to any disclaimer, the term of this patent is extended or adjusted under 35 U.S.C. 154(b) by 0 days.

(21) Appl. No.: 10/364,423

(22) Filed: Feb. 12, 2003

Related U.S. Application Data (63) Continuation of application No. 09/692,322, filed on Oct. 20, 2000, now abandoned.

(51) Int. Cl.[7] ............................. G01N 21/17; G01J 5/00
(52) U.S. Cl. ..................... 250/341.1; 250/330; 250/340
(58) Field of Search .............................. 250/341.1, 330, 250/332, 340

(56) References Cited

U.S. PATENT DOCUMENTS

| | | | |
|---|---|---|---|
| 5,623,145 A | 4/1997 | Nuss | 250/330 |
| 5,710,430 A | 1/1998 | Nuss | 250/330 |

OTHER PUBLICATIONS

Martin van Exter, et al., *Terahertz time–domain spectroscopy of water vapor*, Optics Letters, vol. 14, No. 20, p. 1128–1130 (Oct. 15, 1989).

Q. Wu and X.C. Zhang, *Free–space electro–optic smapling of terahertz beams*, Appl. Phys. Letters, vol. 67, p. 3523–3525 (Dec. 11, 1995).

S. Verghese, et al, *Generation and detection of coherent terahertz waves using two photomixers*, Appl. Phys. Letters, vol. 73, No. 26, p. 3824–3826 (Dec. 28, 1998).

A.S. Weling, et al., *Generation of tunable narrow–band THz radiation from large aperture photconducting antennas*, Appl. Phys. Lett., vol. 67, p. 137–139 (Jan. 10, 1994).

N.M. Froberg, et al., *Generation of steerable submillimeter waves from semiconductor surfaces by spatial light modulators*, Appl. Phys. Lett. vol. 59, p. 768–770 (Aug. 12, 1991).

Y.S. Lee, et al., *Generation of narrow–band terahertz radiation via optical rectification of femtosecond pulses in periodically poled lithium niobate*, Appl. Phys. Lett., vol. 76, No. 18, p. 2505–2507 (May 1, 2000).

Ajay Nahatha, et al., *Free–space electro–optic detection of continuous–wave terahertz radiation*, Appl. Phys. Lett., vol. 75, No. 17, p. 2524–2526 (Oct. 25, 1999).

B.B. Hu and M.C. Nuss, *Imaging with terahertz waves*, Appl. Phys, Lett, vol. 20, No. 16, p. 1716–1718 (Aug. 15, 1995).

Q. Wu, et al., *Two–dimensional electro–optic imaging of THz beams*, Appl. Phys. Lett., vol. 69, p. 1026–1028 (Aug. 19, 1996).

(List continued on next page.)

*Primary Examiner*—Albert Gagliardi
(74) *Attorney, Agent, or Firm*—Sughrue Mion, PLLC (57) ABSTRACT

An invention is described, which uses terahertz radiation for chemical sensing and gas analysis. Relatively narrow-band THz radiation is generated by impinging an optical pulse train from a short-pulse laser source on a THz emitter. Coherent detection of the resulting THz radiation is accomplished by using a similar optical pulse train to activate the THz sensor. The invention is shown to detect and indicate various concentrations of water vapor in air. Optimal phase biasing conditions give maximum sensitivity to variations in concentration of the species under investigation.

26 Claims, 8 Drawing Sheets

OTHER PUBLICATIONS

G. Imeshev, et al., *Engineerable femtosecond pulse shaping by second–harmonic generation with Fourier synthetic quasi–phase–matching gratings*, Opt. Lett., vol. 23, No. 11, p. 864–866 (1998).

C.W. Siders, et al, *Generation and characterization of terahertz pulse trains from biased, large–aperture photconductors*, Opt. Lett., vol. 24, No. 4, p. 241–243 (Feb. 15, 1999).

Richard K. Lai, et al, *A photoconductive, miniature terahertz source*, Appl. Phys. Letter, vol. 72, No. 24, p. 3100–3102 (Jun. 15, 1998).

Q. Wu et al., "Free–space electro–optic sampling of terahertz beams", Appl. Phys. Lett. vol. 67, No. 24, Dec. 11, 1995, pp. 3523–3525.

S. Verghese et al., "Generation and detection of coherent terahertz waves using two photomixers", Appl. Phys. Lett. vol. 71, No. 26, Dec. 28, 1998, pp. 3824–3826.

A.S. Weiling, et al, "Generation of tunable narrow–band THz radiation from large aperture photoconducting antennas", Appl. Phys. Lett. vol. 64, No. 2, Jan. 10, 1994, pp. 137–139.

X–C. Zhang et al, "Generation of steerable submillimeter waves from semiconductor surfaces by spatial light modulators", Appl. Phys. Lett., vol. 59, No. 7, Aug. 12, 1995, pp. 768–770.

Y–S. Lee, et al. "Generation of narrow–band terahertz radiation via optical rectification of femtosecond pulses in periodically poled lithium niobate", Appl. Phys. Lett. vol. 76, No. 18, May 1, 2000, pp. 2505–2507.

A. Nahata et al, "Free–space eletro–optice detection of continuous–wave terahertz radiation", Appl. Phys. Lett. vol. 75, No. 17, Oct. 25, 1999, pp. 2524–2526.

B.B. Hu et al, "Imaging with treahertz waves", Optics Letters, vol. 20, No. 16, Aug. 15, 1995, pp. 4716–4718.

Q. Wu et al, "Two–dimensional electro–optic imaging of THz beams", Appl. Phys. Lett. vol. 69, No. 8, Aug. 19, 1996, pp. 1026–1028.

G. Imshev et al., "Engineerable femtosecond pulse shaping by second–harmonic generation with Fourier synthetic quasi–phase–matching gratings", Optics Letters, vol. 23, No. 11, Jun. 1, 1998, pp. 864–866.

C.W. Siders et al, "Generation and characterization of terahertz pulse trains from biased, large–aperture photoconductors", Optics Letters, vol. 24, No. 4, Feb. 15, 1999, pp. 241–243.

Richard K. Lai et al, "A photoconductive, miniature terahertz source", Appl. Phys. Lett. vol. 72, No. 24, Jun. 15, 1998, pp. 3100–3102.

SINGLE-SHOT DIFFERENTIAL SPECTROSCOPY AND SPECTRAL-IMAGING AT SUBMILLIMETER WAVELENGTHS

This is a continuation of application Ser. No. 09/692,322 filed Oct. 20, 2000 now abandoned; the disclosure of which is incorporated herein by reference.

BACKGROUND OF THE INVENTION

Systems are known in which ultrashort laser pulses are used to generate and coherently detect terahertz (THz) radiation. Most types of THz systems use single laser pulses to generate broad-band THz radiation. Time-domain, terahertz spectroscopy has been shown to provide a useful analytical tool for measuring properties of molecular vapors, both pure and in mixture with other gases, such as air (see M. van Exter, et al., Optics Letters, Vol 14, p. 1128 (1989)). The use of THz radiation reveals certain features which are not afforded by the use of laser radiation lying in the "usual" range of 200 nm to 10 microns.

X. -C. Zhang et al., teach a THz sensing system which employs electro-optic crystals, such as ZnTe, to serve as THz receivers, these having the advantage of higher detection bandwidth (see Q. Wu and(X. -C. Zhang, Appl. Phys. Lett, Vol 67, p. 2523 (1995)). The generation of narrow-band THz radiation can give significant advantages over broad-band THz generation in certain spectroscopic applications. Continuous wave narrow-band THz radiation can be generated and detected by photomixing two CW lasers in a THz transceiver, such as a photoconductive antenna, as demonstrated by Verghese et al. (see S. Verghese, et al., Appl. Phys. Lett, Vol. 73, p. 3824 (1998)). Moderately narrow-band THz bursts can be generated by exciting a THz emitter with a train of optical pulses spaced to the desired THz frequency as taught by Siders et al. (see C. W. Siders, et al., Opt. Lett., Vol 24, p. 241 (1999)), and Weling et al. who excites a semiconductor surface (see A. S. Weling, et al., Appl. Phys. Lett., Vol. 64, p. 137 (1994)). Alternatively, Norris demonstrates a method in which a single laser pulse can be used to generate narrow-band THz radiation directly by optical rectification in a periodically poled nonlinear crystal such as PPLN (periodically poled lithium niobate), by exploiting the group-velocity walkoff between the optical pulse and the THz radiation in the crystal (see T. -S. Lee, T. Meade, V. Perlin, H. Winful, T. B. Norris, A. Galvanauskas, "Generation of narrow-band terahertz radiation via optical rectification of femtosecond pulses in periodically poled lithium niobate," Appl. Phys. Lett., Vol. 76, p. 2505 (2000)). In another method which does not employ ultrafast lasers, T. Heinz et al. teach a THz generation/detection system employing two detuned CW lasers to generate THz radiation at the beat frequency between the two lasers (see A. Nahatha, James T. Yardley, Tony, F. Heinz, "Free-space electro-optic detection of continuous-wave terahertz radiation," Appl. Phys. Lett., Vol. 75, p. 2524 (1999)). The same two lasers activate the THz receiver, providing narrow-band coherent detection. This system provides very narrow-band THz radiation with ~MHz linewidths, limited only by the absolute frequency stability of the two CW lasers, and have potential for linewidths less than 1 kHz.

CW heterodyne methods provide superior frequency resolution in the THz measurement system, however suffer the drawbacks of very low efficiency, as well as fringe ambiguity. While these systems can give sub-wavelength resolution, the larger scale TOF (time-of-flight) information is lost. The use of ultrashort pulses to generate and detect THz radiation provides useful TOF information. Furthermore, the use of ultrashort pulses can ultimately result in greater efficiency of THz emission, especially in cases such as that demonstrated by Norris, where the optical pulse is re-used many times in the generation process. As extensions of the THz sensing technology, various systems have been devised which combine THz generation/detection with imaging to give imaging in the THz frequency range. B. Hu et al. teach a THz imaging system which uses single, broad-band THz pulses repetitively while the sample under test is raster scanned through the THz beam (see B. B. Hu and M. C. Nuss, Appl. Phys. Lett, Vol. 20, p. 1716 (1995); see U.S. Pat. No. 5,623,145; and see U.S. Pat. No. 5,710, 430). Because this system relies on THz waveform measurement, time delay scanning was required in addition to the raster scanning, both techniques, in turn, requiring the use of a large number of laser shots to complete the measurement even if no signal averaging was used. This type of system generally requires at least several minutes to complete an imaging measurement. Additionally, if spectral information about the image is desired, then complex signal analysis such as Fourier or wavelet transforms are required. A system for performing THz imaging with a single laser shot was first demonstrated by Q. Wu et al. This system works by using an EO field sensor crystal to impart THz image information on an optical beam (an ultrashort laser pulse), and then imaging the optical beam with an optical imaging device such as a CCD camera (see Q. Wu, T. D. Hewitt, and X. -C. Zhang, Appl. Phys. Lett., Vol. 69, 1026 (1996)).

SUMMARY OF THE INVENTION

The current invention combines advantages of tunable narrow-band THz generation and coherent detection, with the unique properties of ultrashort pulses, those being single-shot capability, TOF information, high pulse intensity, and greater efficiency of THz generation. The current invention provides the additional advantage of using two THz frequencies to give a differential measurement providing greatly enhanced sensitivity and immunity to laser fluctuations. Additionally, the narrowband THz emission can be adapted to single-shot THz imaging systems, which commonly use only a single, broadband THz pulse.

DETAILED DESCRIPTION OF THE PREFERRED EMBODIMENTS

Figure 1:
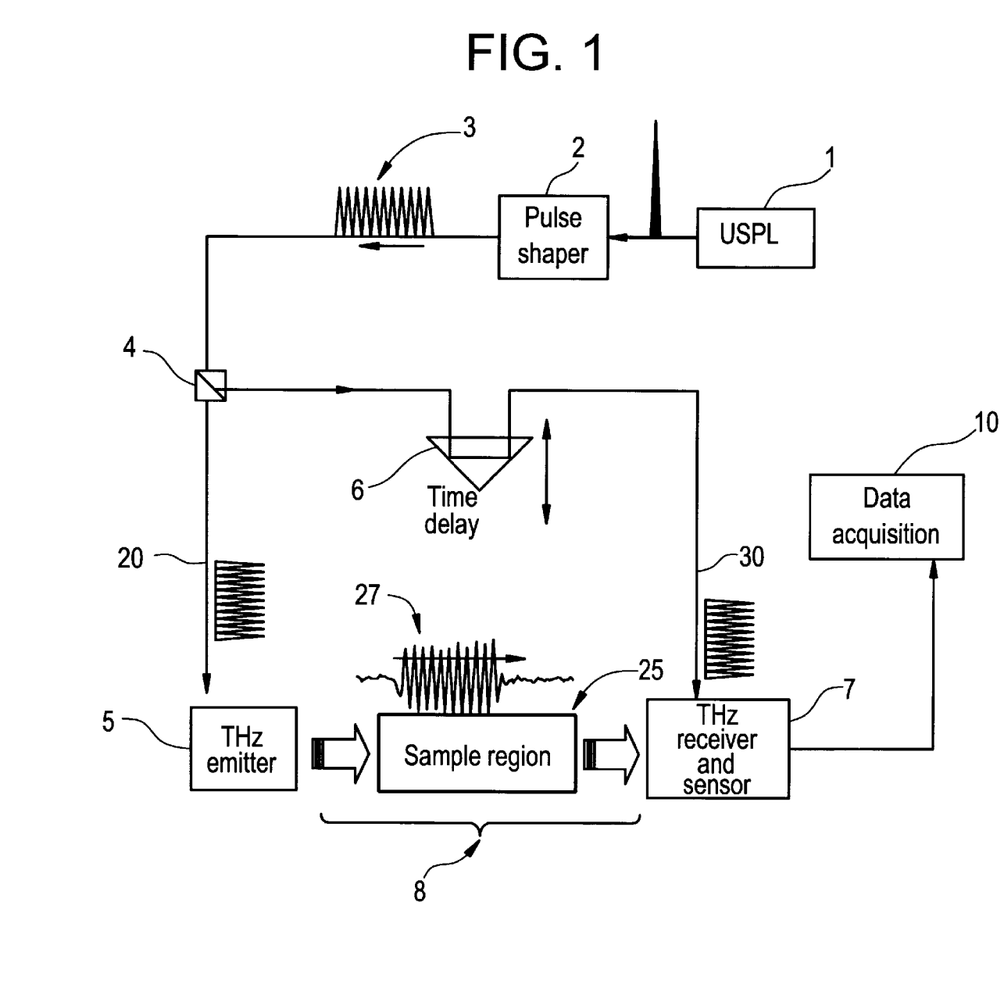
FIG. 1 shows a simplified block diagram of an illustrative narrow-band THz chemical sensing system in accordance with the principles of the present invention.

FIG. 1 illustrates one embodiment of the invention. A single short pulse of optical radiation obtained from an ultrashort pulse laser (USPL) 1 is converted, by a pulse shaper 2, into a sequence of optical pulses 3, separated by time intervals which are substantially equal. The repetition frequency of the pulse train is chosen to correspond to the desired Terahertz frequency. In the preferred embodiment, the pulse shaper is a quasi-phase matched nonlinear optical crystal—such as periodically poled lithium niobate (PPLN)—which is constructed with multiple poled zones, so as to produce a train of frequency doubled pulses from a single optical pulse, as taught by Galvanauskas, et al. (see G. Imeshev, A. Galvanauskas, D. Harter, M. A. Arbore, M. Proctor, and M. M. Fejer, "Engineerable femtosecond pulse shaping by second-harmonic generation with Fourier synthetic quasi-phase-matching gratings," Opt. Lett., Vol. 23, p. 864 (1998)). In general, the pulse shaper need not frequency double the input. The pulse shaper could also be based on diffraction gratings and spatial light modulators, as taught by Weiner (see C. W. Siders, et al, Opt. Lett., Vol. 24, p. 241 (1999)). The optical pulse train is split into two paths by a beam splitter 4; one beam 20 impinging on a THz emitter 5, and the other beam 30 being passed through a controllable optical delay 6 and subsequently impinging on a THz receiver 7. The THz emitter and receiver are configured with intervening optical elements (not, shown), so that THz radiation from the emitter propagates through a free-space path 8, and then is incident on the receiver 7 where it is detected. If desired, a gas cell or other sample holder 25 is placed in this free-space path so that the THz radiation passes through it. The receiver is activated and gated by the delayed optical pulse train 30. If the sum of the optical path lengths of the input (pump) beam path 20 and the free space THz beam path 8 is substantially equal to the path length of the delayed gating beam 30, then the transmitted THz waveform 27 from emitter 5 and the optical gating waveform 30 will substantially coincide in time upon arrival at the THz sensor 7, giving the necessary temporal overlap to effect THz detection. The end-result of this measurement (which may be output to a data acquisition device 10) is a single value of signal level obtained from the THz detection system, which will depend upon the amplitude of the THz emitter beam 27, and on the precise timing delay between the THz emitter waveform (as affected by sample 25) and the gating optical pulse train 30. Because no time delay scanning is required, this measurement can be effected using a single laser shot, or with multiple laser shots if signal averaging is desired.

Figure 2:
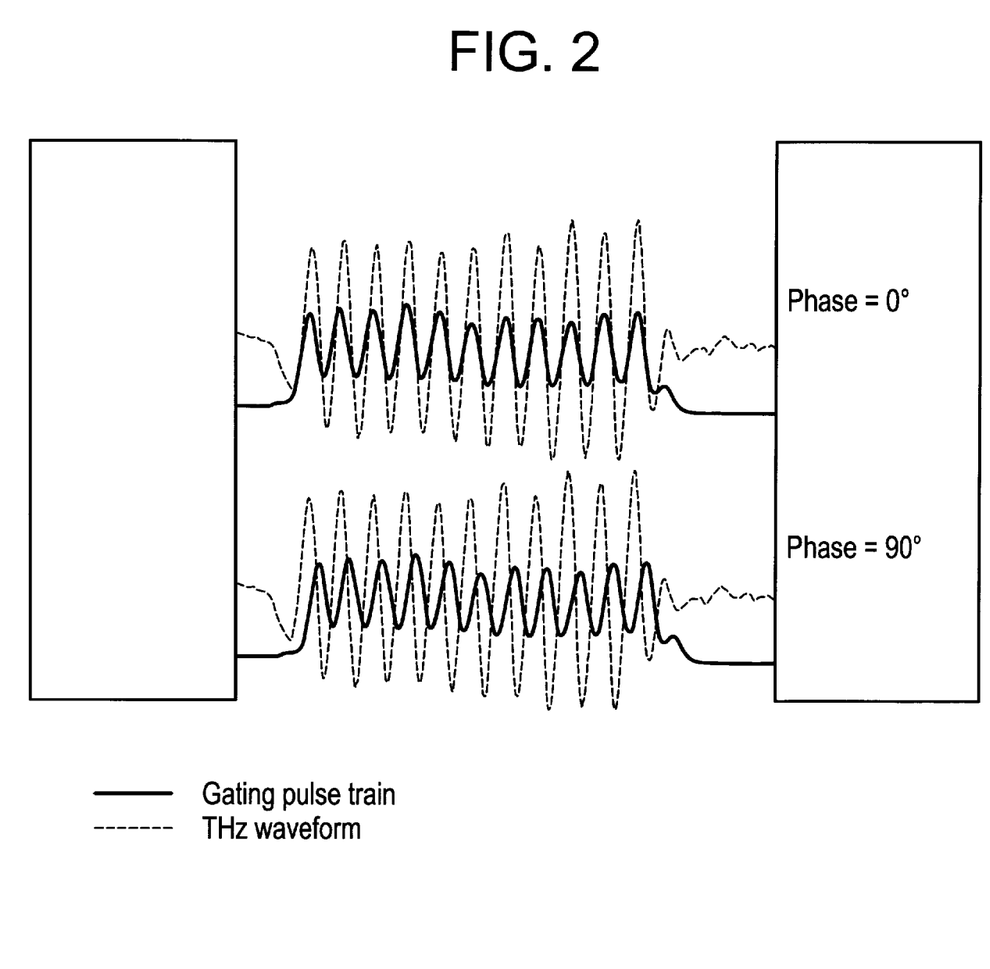
FIG. 2 shows comparisons between THz waveforms and the optical gating waveforms, illustrating the relative phase between them.

Because the transmitted THz waveform 27 and the optical gating waveform pulse train 30 have essentially the same frequency, this effectively provides a form of matched filtering during the detection process. From this nominally pathlength-matched condition, small adjustments can be made in the time delay of the gating pulse train 30, such that the THz phase between the THz waveform 27 and gating pulse train 30 can be adjusted anywhere in the range of 0 to 360 degrees, as illustrated in FIG. 2. In this way, the system can be phase-biased to provide maximum sensitivity to changes in either amplitude or phase of the THz waveform 27. Amplitude sensitivity is maximized by setting the phase to either 0 or 180 degrees. Phase sensitivity is maximized by setting the phase to either 90 or 270 degrees. If the THz beam 27 encounters primarily a change in either index of refraction or path length in the intervening sample medium, the change being smaller than the nominal THz wavelength, then it is advantageous to bias the phase near 90 or 270 degrees. If the THz beam encounters a significant absorption in the sample medium, which would effect primarily a change in amplitude, then it is advantageous to bias the phase near 0 or 180 degrees. Under certain conditions (e.g., resonantly absorptive media) both the amplitude and phase of the THz waveform are changed by propagating through the sample medium, so that the optimal phase condition will deviate from the previously stated values of 0, 90, 180, or 270 degrees.

Figure 3A:
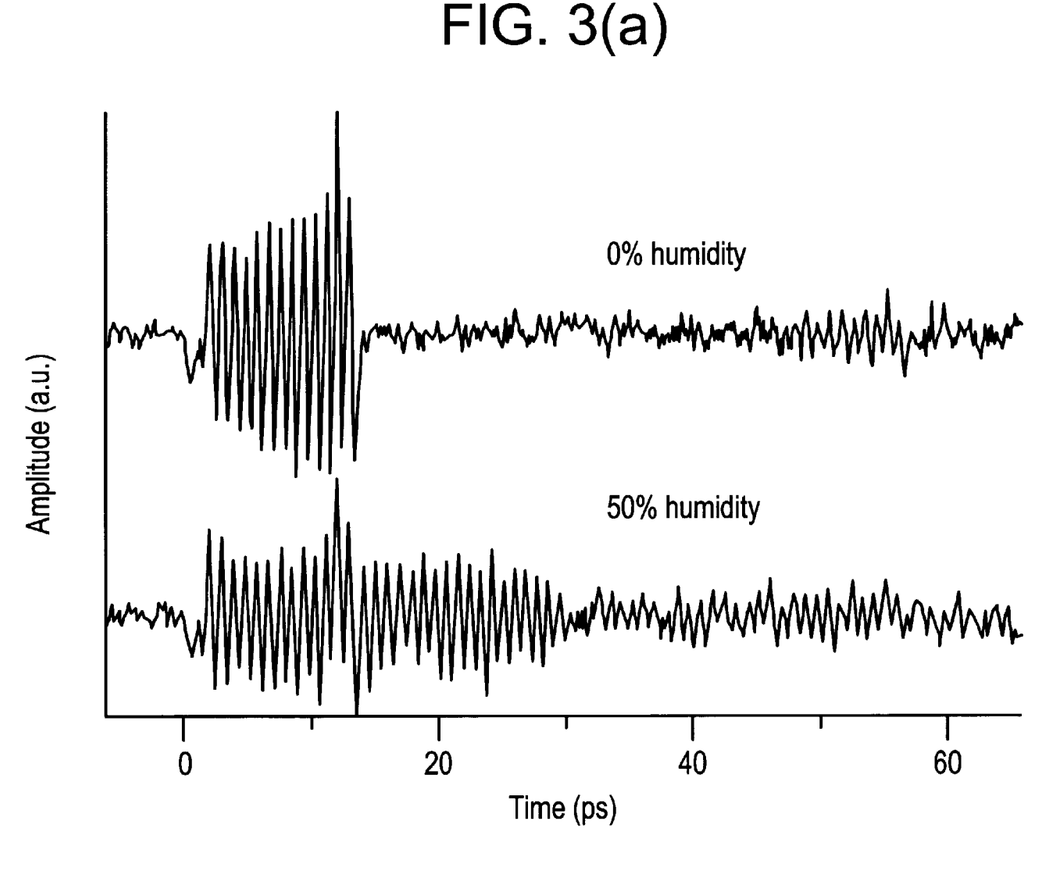
FIG. 3(a) shows a transmitted THz waveform after propagation through a sample space filled with dry air (upper trace) and air with 50% humidity (lower trace), illustrating the effect of free induction decay when the THz waveform is tuned in resonance with the water vapor absorption.
Figure 3B:
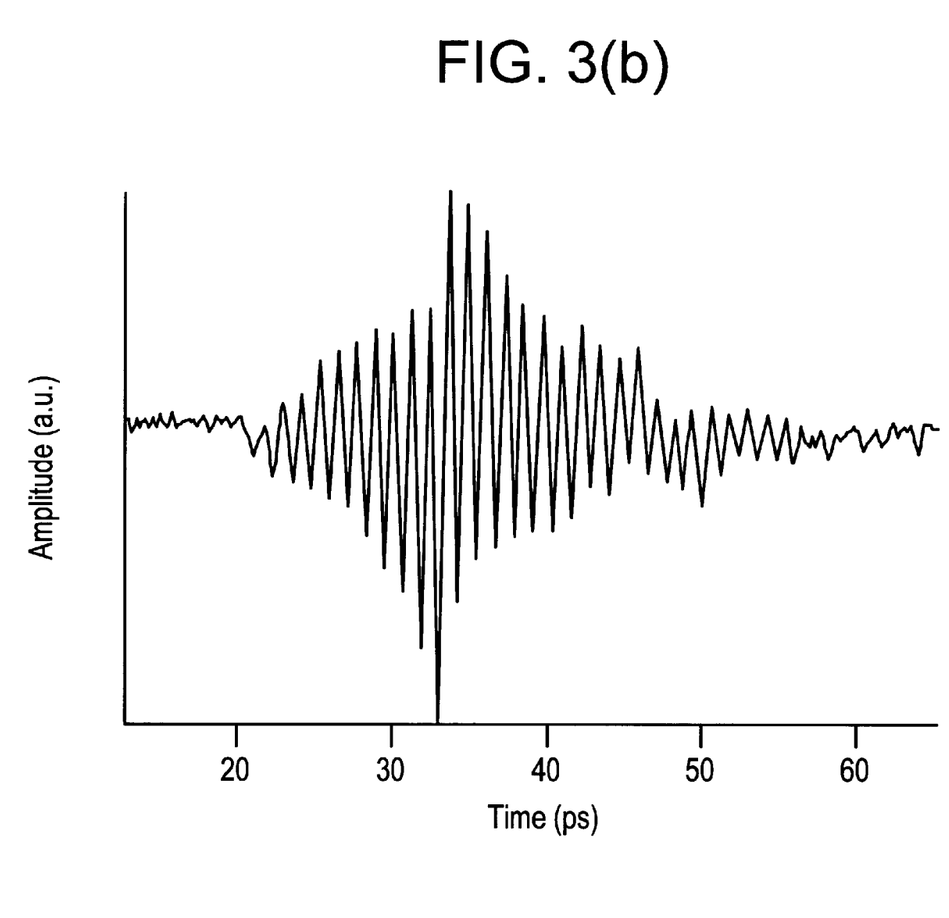
FIG. 3(b) shows a cross-correlation between the transmitted THz waveform and the optical gating pulse, illustrating the effects of phase, and the asymmetry due to free induction decay.
Figure 4:
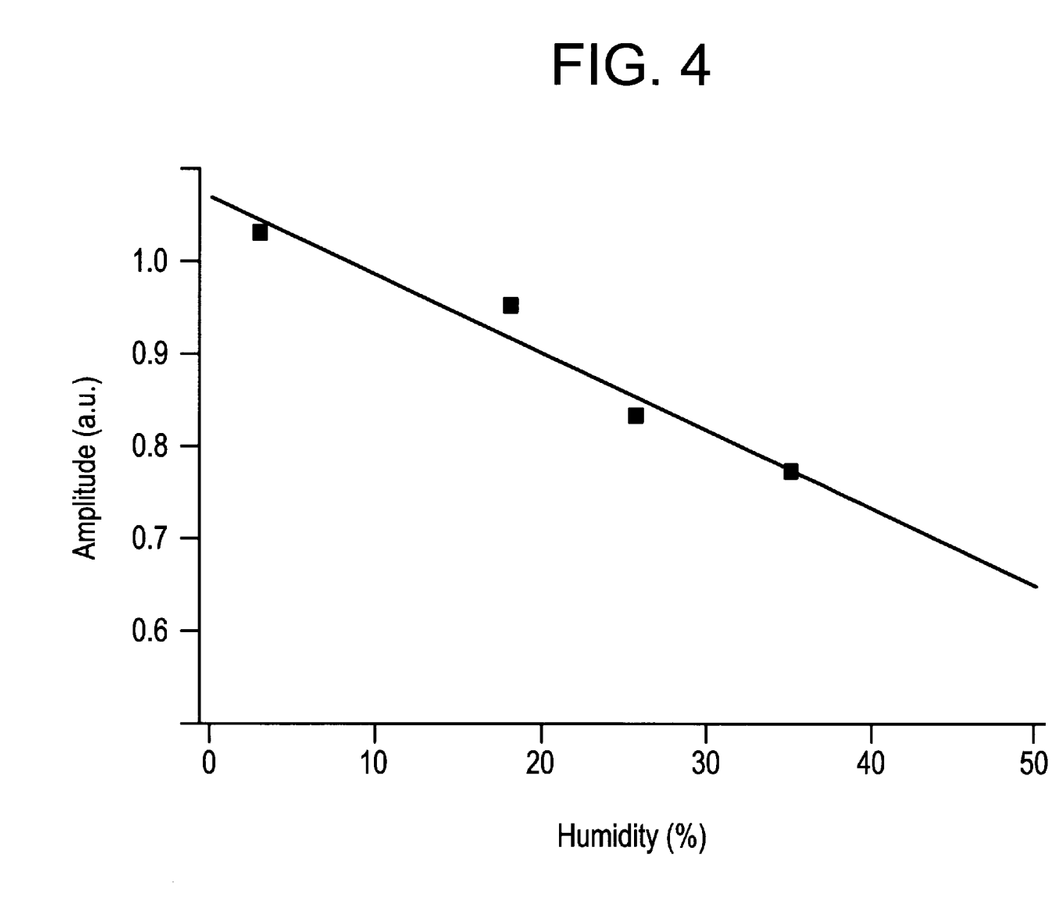
FIG. 4 shows the output signal of the THz sensing system when the sample space contains air of varying levels of relative humidity.

After propagating through a resonantly absorbing medium, the transmitted THz waveform will be followed by radiation due to free induction decay (FID), and the resulting distortion of the original pulse, as has been shown by Grischkowsky when using a single broadband THz pulse (see M. van Exter, et al., Optics Letters, Vol 14, p. 1128 (1989)). A similar effect also occurs when using a narrowband THz burst, and is illustrated in FIG. 3($a$). The optimum phase bias for detection can by found in advance of the real measurement by performing calibration scans of known species at known concentrations, such a scan being shown in FIG. 3($b$). Under the optimal phase bias conditions, the resulting output signal level will depend on the concentration of the species in the THz beam paths, a higher concentration giving a higher or lower signal level, depending upon the relative phase. FIG. 4 shows a plot of signal level as a function of vapor concentration (relative humidity) for a THz detection system which was tuned to the water vapor resonance at 1.09 THz.

Furthermore, instead of sampling the difference in amplitude of the propagated beam, an amplitude of the free induction decay can be measured.

THz DIA (Differential Absorption) System

Figure 5:
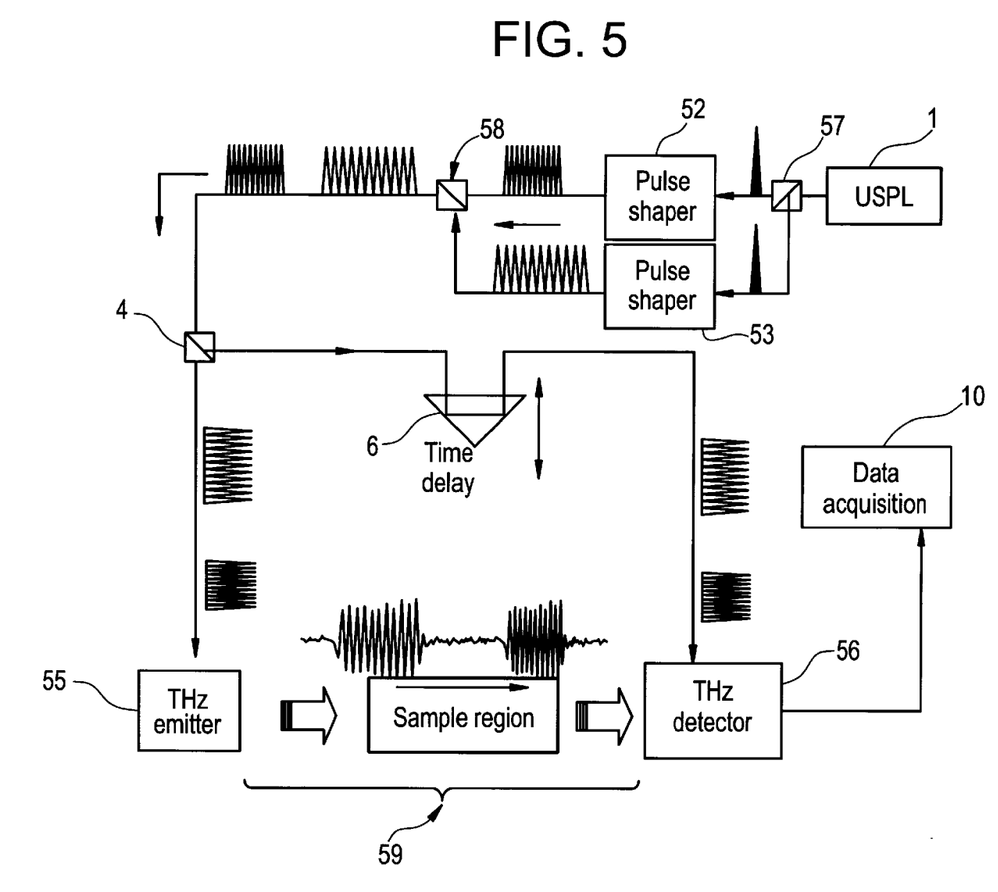
FIG. 5 shows an illustrative THz DIA (differential absorption) system in which THz pulse bursts of two different frequencies are generated, are propagated through the sample-region, and are then coherently detected.

Another embodiment of the invention is shown in FIG. 5, where two nonlinear optical pulse shapers 52 and 53 (which convert optical radiation obtained from USPL 1 via a beam splitter 57) are used together simultaneously with a single THz emitter 55, and a single THz detector 56. The pulse shaper could be similar to those described by Weling et al. and by Siders et al. The first pulse shaper 52 is tuned so that the first THz waveform coincides with an absorption resonance of the species under study, while the second pulse shaper 53 is adjusted so that the second THz waveform does not coincide with this absorption resonance (the output beam paths of the first pulse shaper and the second pulse shaper are combined at 58). There is a substantial time delay (>1 ns) between the two THz waveforms. Separate detection of the two THz frequencies is obtained by time-gating the data acquisition properly, requiring that the time delay between the THz waveforms be on the order of 1 ns or greater (according to state of the art acquisition systems). Using two THz frequencies simultaneously gives much greater immunity to laser noise, and therefore much greater sensitivity. This is similar in principle to the well known technique of differential absorption lidar (DIAL); however, according to the invention it is performed in the THz frequency region, which is not covered by lasers.

In yet another embodiment of the invention, two separate THz emitters, and two separate THz detectors could be used, one for each THz frequency. In this type of system, one would still have to insure that the two THz beams pass through the same sample region 59; however, the ns order delay between the THz pulse trains could be dispensed with. This system has the advantage that phase variations from thickness variations of the sample material would have smaller effects on the error in measurement. The non-absorbed signal can be used to correct the phase.

Narrow-band THz Imaging

Figure 6:
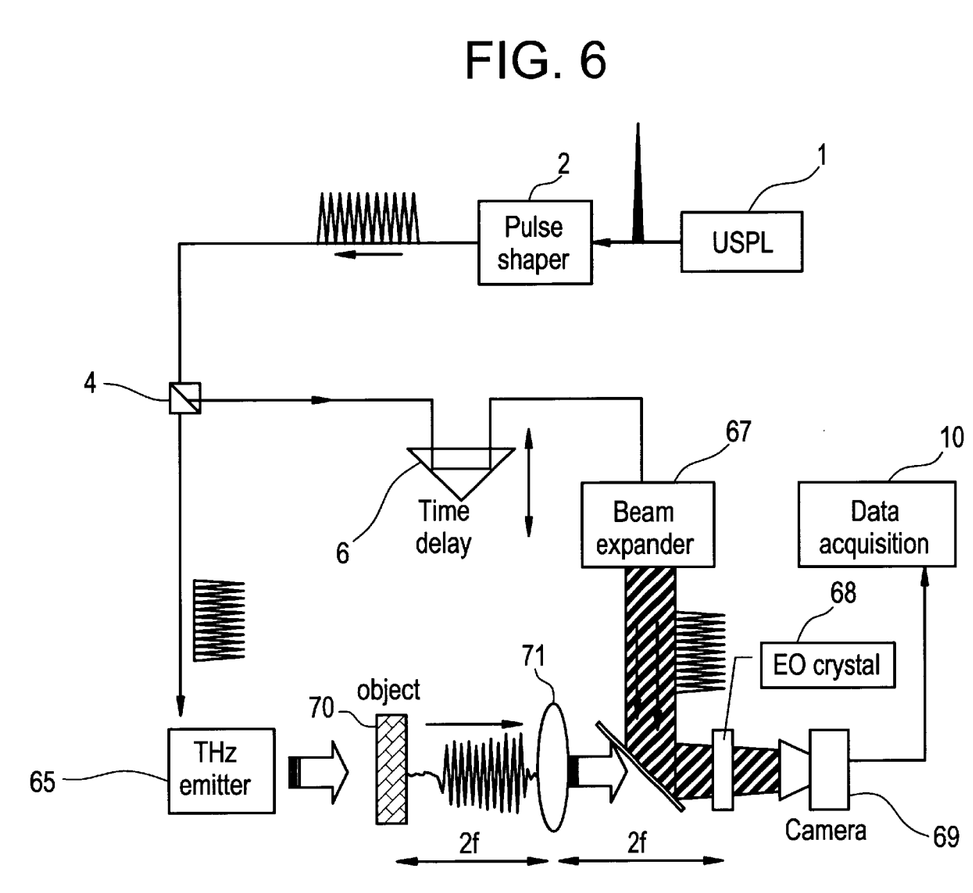
FIG. 6 shows an illustrative example of a single-shot THz imaging system which employs narrowband THz radiation and matched filter detection.

The above-described systems use a single THz detector for the (or each) THz beam, which has the effect of spatially integrating over the profile of the THz beam. This effectively discards any spatial information imparted to the THz beam by local variations in the sample under test. However, this narrow-band THz technique can be combined with single-shot THz imaging, as illustrated in FIG. 6. The invention employs an ultrashort pulse laser emitting a single optical pulse, which is passed through pulse shaper 2 to obtain the pulse train. This signal is split; one portion used to activate the emitter 65, while the other portion passes through an electro-optic sensor crystal 68, via, for example, a beam expander 67. Both the THz emitter input pulse and the expanded optical pulse pass through the EO crystal 68 simultaneously (an imaging lens 71, arranged between object 70 and EO crystal 68, may be deployed along the path of the THz emitter pulse), whereby any spatial information from the THz beam is imparted to the expanded optical beam by modification of the polarization properties of the expanded optical beam across its spatial profile. The resultant optical beam is then sent through polarizing optics (not shown), and finally to an imaging device such as a CCD camera 69, which then records the resulting imposed intensity variations. In the current state of the art, this measurement is done with a single broadband THz pulse, which gives limited spectral information. However, by using trains of ultrashort pulses for generation and detection, as described in this invention, it is possible to obtain single-shot THz imaging at a specific THz frequency, thus giving the capability of hyper-spectral imaging at particular THz wavelengths. This provides an enhancement in functionality over the single-shot, broadband THz imaging shown, for example, by Wu et al. (see Q. Wu and X. -C. Zhang, Appl. Phys. Lett, Vol 67, p. 2523 (1995)). Additionally, the spectral image information is obtained without the need for complex signal processing such as Fourier or wavelet transforms.

Figure 7:
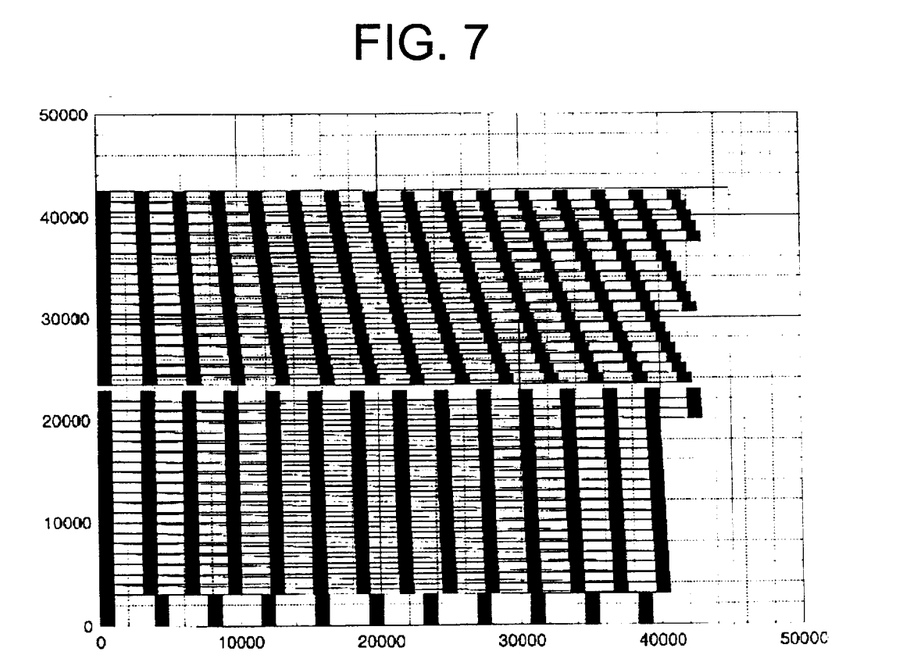
FIG. 7 shows a schematic design of a tunable quasi-phase-matched nonlinear optical device for generation of frequency-converted pulse sequences from a single input pulse.

FIG. 7 shows a schematic design of a tunable quasi-phase-matched nonlinear optical device for generation of frequency-converted pulse sequences from a single input pulse. The tunability is designed into the structure by a lateral variation in the spacing between the poled regions of the device, and the tunability of the pulse repetition frequency is effected by laterally positioning the input pulse to propagate along one of the several poled regions. By changing the position of the frequency doubled sections it is also possible to achieve a variation of the phase delay.

For example, referring to FIG. 7, the region with "tilted" poled region affects the phase delay. Furthermore, the poled regions may be "tilted" the same amount such that the difference between all "tilted" poled regions is constant.

It is understood that the invention described here is not limited to the specific embodiments described above, but that many variations in the invention can be implemented, but which would still fall within the spirit of the invention.

What is claimed is:

1. An apparatus, for generating narrowband THz waveforms, comprising:
   an ultrashort pulse laser;
   a pulse-shaping device which receives an output of said ultrashort pulse laser and generates an optical pulse train at an optical wavelength different from a wavelength of said output; and
   a THz emitter which is excited by said optical pulse train.

2. An apparatus as claimed in claim 1, wherein the pulse-shaping device comprises a multiple-zoned, quasi-phase matched nonlinear crystal.

3. An apparatus as claimed in claim 2, wherein the multiple-zoned, quasi-phase matched nonlinear crystal is one of PPLN and PPKTP.

4. An apparatus as claimed in claimed in claim 1, further comprising:
   a narrowband THz sensor;
   a beam delivery system which receives said optical pulse train generated by said pulse-shaping device and outputs said optical pulse train to the THz emitter and the THz sensor; and
   an adjustable phase delay for adjusting the THz pulses emitted from the THz emitter with respect to an intensity envelope phase of said optical pulse train incident on the THz sensor;
   wherein the ultrashort pulse laser excites both the THz emitter and the THz sensor, and the THz beam generated by the THz emitter impinges on the THz sensor.

5. An apparatus as claimed in claim 1, wherein the pulse-shaping device is a pulse-shaping frequency converter.

6. An apparatus as claimed in claim 1 wherein said beam delivery system comprises a beam splitter.

7. An apparatus as claimed in claim 1, wherein said pulse shaping device comprises a large-aperture photoconducting antenna.

8. An apparatus as claimed in claim 1, wherein said pulse shaping device comprises an $2^n$-pulse Michelson interferometer.

9. An apparatus for coherently sensing narrowband THz waveforms, comprising:
   an ultrashort pulse laser;
   a pulse shaper which converts a single optical pulse into a THz pulse train; and
   a THz sensor which is activated by said pulse train.

10. An apparatus as claimed in claim 9, wherein said THz sensor is an electro-optic sensor comprising a ZnTe crystal; or other EO crystal (including, but not limited to GaAs, DAST, InP, $LiTaO_3$, InAs); or a photoconducting dipole antenna.

11. A method for coherent detection of narrowband THz radiation comprising:
   generating a sequence of ultrashort optical pulses at a THz repetition rate; and
   effecting detection of the THz radiation by the sequence of ultrashort optical pulses.

12. A method of chemical analysis employing a narrowband THz sensing system comprising:
   generating ultrashort laser pulses;
   receiving said ultrashort laser pulses and generating an optical pulse train at an optical wavelength different from a wavelength of said ultrashort laser pulses;
   exciting a THz emitter by said optical pulse train;
   outputting said optical pulse train to the THz emitter and a narrowband THz sensor;

and adjusting THz pulses emitted from the THz emitter with respect to an intensity envelope phase of said optical pulse train incident on the THz sensor;

wherein the ultrashort laser pulses excite both the THz emitter and the THz sensor, and a THz beam generated by the THz emitter impinges on the THz sensor;

said method further comprising passing the THz beam generated by the THz emitter through a sample region containing at least one chemical species, and determining a property of said chemical species from at least one of (1) analysis of said THz beam after passage through said sample region and (2) a radiation, which follows said THz beam, due to free induction decay.

13. A method of chemical analysis, as claimed in claim 12, further comprising, after said receiving of said ultrashort laser pulses and said generating of said optical pulse train, tuning said optical pulse train to an absorption resonance of the chemical species.

14. A method of chemical analysis as claimed in claim 12 further comprising setting an optimal phase bias condition such that an amplitude of said THz beam after passing through said sample region is dependent on a concentration of said chemical species.

15. A method of chemical analysis as claimed in claim 14 wherein a higher concentration of said chemical species results in a higher or lower amplitude of said THz beam depending upon a relative phase.

16. A method of chemical analysis as claimed in claim 12 wherein said determination further comprises determining a concentration of said chemical species based on said analysis of said radiation due to free induction decay.

17. An apparatus comprising:
an ultrashort pulse laser;
a first pulse shaper;
a second pulse shaper separate from said first pulse shaper;
a first THz emitter transmitting a first THz beam along a first THz beam path;
a second THz emitter, separate from said first THz transmitter, transmitting a second THz beam along a second THz beam path, distinct from said first THz beam path;
a first THz sensor; and
a second THz sensor, separate from said first THz sensor, wherein said first THz emitter and said first THz sensor are excited by an optical pulse train from said first pulse shaper, and said second THz emitter and said second THz sensor are excited by an optical pulse train from said second pulse shaper.

18. A method for chemical sensing using a two-frequency THz apparatus comprising: an ultrashort pulse laser; a first pulse shaper; a second pulse shaper separate from said first pulse shaper; a first THz emitter transmitting a first THz beam along a first THz beam path; a second THz emitter, separate form said first THz transmitter, transmitting a second THz beam along a second THz beam path, distinct from said first THz beam path; a first THz sensors; and a second THz sensors, separate from said first THz sensor, wherein said first THz emitter and said first THz sensor are excited by an optical pulse train from said first pulse shaper, and said second THz emitter and said second THz sensor are excited by an optical pulse train from said second pulse shaper, said method comprising:

passing THz beams generated by said first and second THz emitters through a sample region containing a chemical species tuning one of said first and second THz emitters to an absorption resonance of the chemical species; and tuning another of said first and second THz emitters away from any absorption resonance of the chemical species, detecting the signals from each of the two THz sensors, and measuring the difference or normalized difference between the signals, and determining a property of the chemical species in said sample from said difference.

19. An apparatus for imaging narrowband THz radiation comprising:
an ultrashort pulse laser;
a pulse-shaping frequency converter which receives an output of said ultrashort pulse laser and generates a pulse train at an optical wavelength different from a wavelength of said output;
a narrowband THz emitter which is excited by said optical pulse train;
a THz field sensor;
polarization optics which modify the polarization properties of the pulse train after the pulse train passes through the THz field sensor; and
an imaging device.

20. An apparatus as claimed in claim 19, wherein said narrowband THz field sensor is an electro-optic sensor comprising a ZnTe crystal; or other EO crystal (including, but not limited to GaAs, DAST, InP, $LiTaO_3$, InAs); or a photoconducting dipole antenna.

21. An apparatus as claimed in claim 19, wherein said imaging device is a CCD camera.

22. An apparatus for generation of frequency-converted pulse sequences from a single input pulse, said apparatus comprising a tunable quasi-phase-matched nonlinear optical device in which:

a tunability of a pulse repetition frequency is designed into a structure of said tunable quasi-phase-matched nonlinear optical device by a lateral variation in spacing between poled regions of said tunable quasi-phase-matched nonlinear optical device, and a tunability of a pulse repetition frequency is effected by laterally positioning an input pulse to propagate along one of a plurality of the poled regions.

23. A method of chemical analysis comprising:
generating ultrashort wavelength laser pulses;
generating an optical pulse train at an optical wavelength different from a wavelength of said ultrashort wavelength laser pulses;
exciting an emitter by said optical pulse train;
passing said optical pulse train excited by said emitter through a sample region containing at least one chemical species; and
determining a property of said chemical species from analysis of at least one of (1) said beam passed through said sample region, and (2) a radiation, which follows said beam, due to free induction decay.

24. A method of chemical analysis as claimed in claim 23 further comprising setting an optimal phase bias condition such that an amplitude of said beam passed through said sample region is dependent on a concentration of said chemical species.

25. A method of chemical analysis as claimed in claim 24 wherein a higher concentration of said chemical species results in a higher or lower amplitude of said beam depending upon a relative phase.

26. A method of chemical analysis as claimed in claim 23, wherein said determination further comprises determining a concentration of said chemical species based on said analysis of said radiation due to free induction decay.

* * * * *